United States Patent
Toita et al.

(10) Patent No.: US 11,249,015 B2
(45) Date of Patent: Feb. 15, 2022

(54) CHEMICAL CONCENTRATION MEASUREMENT APPARATUS

(71) Applicant: Crystal IS, Inc., Green Island, NY (US)

(72) Inventors: Masato Toita, Latham, NY (US); James Davis, Troy, NY (US)

(73) Assignee: Crystal IS, Inc., Green Island, NY (US)

( * ) Notice: Subject to any disclaimer, the term of this patent is extended or adjusted under 35 U.S.C. 154(b) by 0 days.

(21) Appl. No.: 16/894,206

(22) Filed: Jun. 5, 2020

(65) Prior Publication Data

US 2020/0386675 A1  Dec. 10, 2020

Related U.S. Application Data

(60) Provisional application No. 62/858,186, filed on Jun. 6, 2019.

(51) Int. Cl.
*G01J 3/00* (2006.01)
*G01N 21/33* (2006.01)
*G01N 33/18* (2006.01)

(52) U.S. Cl.
CPC ........... *G01N 21/33* (2013.01); *G01N 33/182* (2013.01); *G01N 2201/062* (2013.01); *G01N 2201/0633* (2013.01); *G01N 2201/06113* (2013.01)

(58) Field of Classification Search
CPC .. G01N 21/314; G01N 21/33; G01N 21/3504; G01J 3/10; G01J 3/42
USPC .......................................................... 356/51
See application file for complete search history.

(56) References Cited

U.S. PATENT DOCUMENTS

| 7,372,039 B2 | 5/2008 | Tokhtuev et al. |
| 9,322,772 B2 | 4/2016 | Ehring et al. |
| 2012/0292522 A1 | 11/2012 | Reger |

FOREIGN PATENT DOCUMENTS

| JP | 5665377 B2 | 2/2015 |
| WO | 2002/001198 A1 | 1/2002 |

OTHER PUBLICATIONS

[No Author Listed] UVC LEDs for Environmental Monitoring, Brochure, Crystal IS, Inc., 2014 (8 pages).

(Continued)

*Primary Examiner* — Md M Rahman
(74) *Attorney, Agent, or Firm* — Nutter McClennen & Fish LLP

(57) ABSTRACT

A chemical measurement device for determining the concentration of given chemical in a given fluid has at least one LED light source and at least one light detector. The given chemical has a light absorption curve with a peak, and the at least one LED light source and at least one light detector are configured to collaborate to produce two light signals having peak wavelengths between about 5 nm and 35 nm apart. The two light signal peak wavelengths are in the ultraviolet region with wavelengths beyond the light absorption curve peak. The light signal peak wavelengths, however, also are before the light absorption curve is negligible. The device also has a concentration calculator operatively coupled with the at least one light detector. The concentration calculator is configured to compare the two light signals to produce a concentration signal representing the concentration of the given chemical in the given fluid.

20 Claims, 7 Drawing Sheets

(56) References Cited

OTHER PUBLICATIONS

Halasinski, et al., "Investigation of the Ultraviolet, Visible, and Near-Infrared Absorption Spectra of Hydrogenated Polycyclic Aromatic Hydrocarbons and Their Cations," The Astrophysical Journal, vol. 628, 2005, pp. 555-566.

Pellerin, et al., Optical Techniques for the Determination of Nitrate in Environmental Waters: Guidelines for Instrument Selection, Operation, Deployment, Maintenance, Quality Assurance, and Data Reporting: U.S. Geological Survey Techniques and Methods 1-D5, 2013 (48 pages).

Zhang, et al., "A 271.8 nm deep ultraviolet laser diode for room temperature operation," Applied Physics Express vol. 12, 2019 (4 pages).

International Search Report and Written Opinion for International Application No. PCT/US2020/036396, dated Aug. 27, 2020 (13 pages).

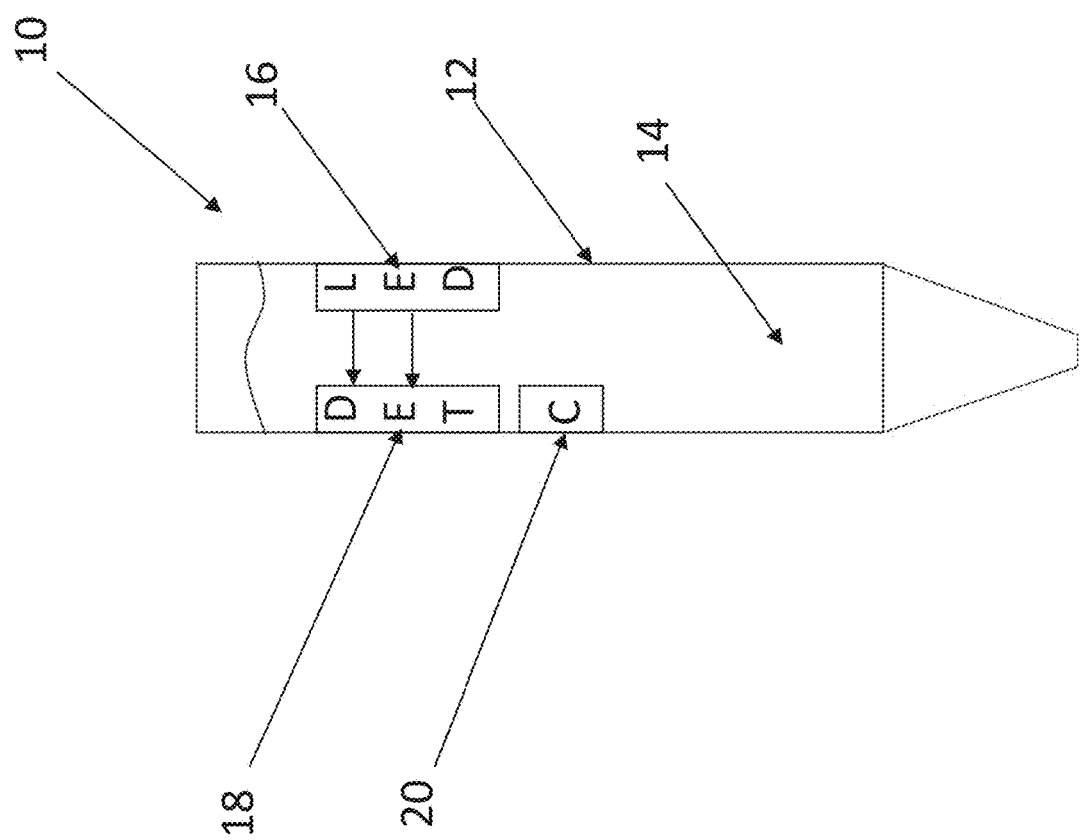

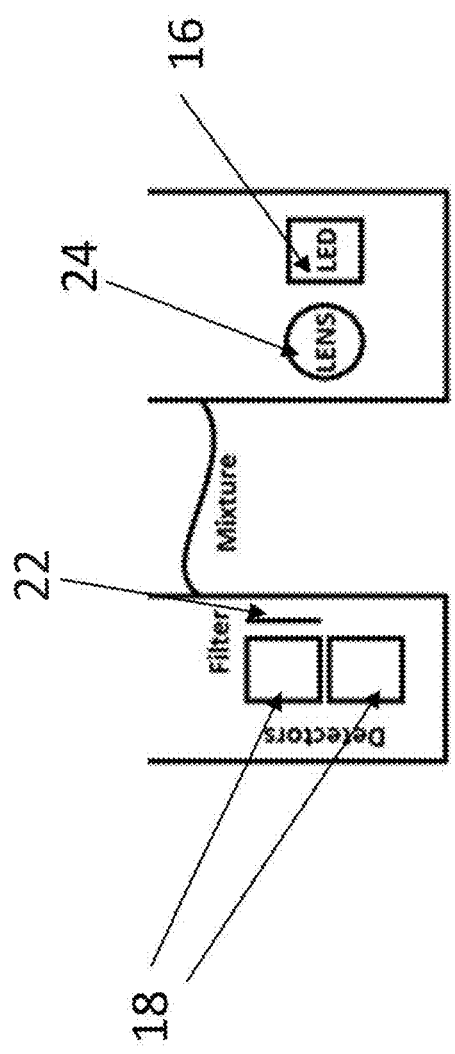
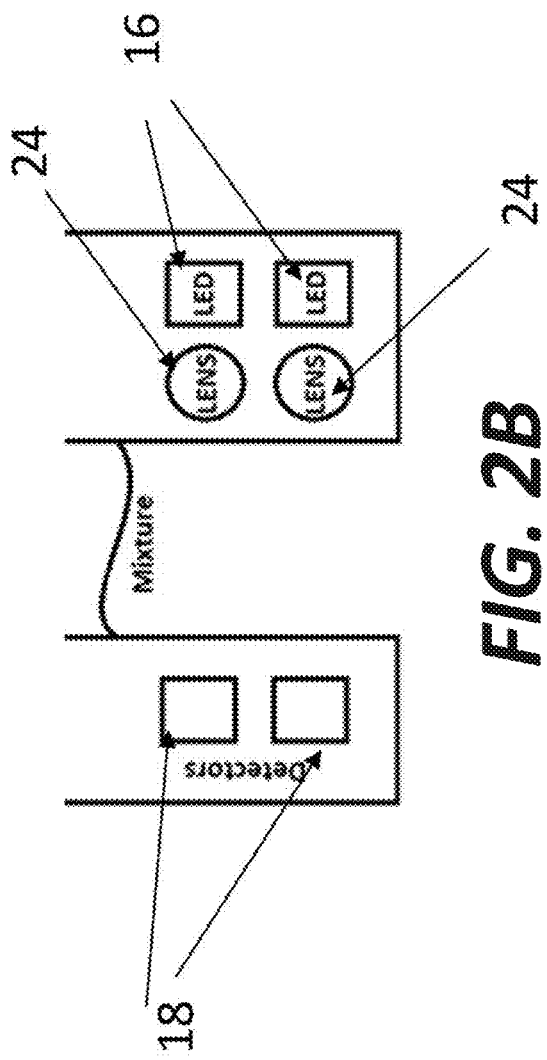
FIG. 2A
FIG. 2B

CHEMICAL CONCENTRATION MEASUREMENT APPARATUS

PRIORITY

This patent application claims priority from provisional U.S. patent application No. 62/858,186, filed Jun. 6, 2019, entitled "CHEMICAL CONCENTRATION MEASUREMENT APPARATUS," and naming Masato Toita, and James Davis as inventors, the disclosure of which is incorporated herein, in its entirety, by reference.

FIELD OF THE INVENTION

Illustrative embodiments of the invention generally relate to determining chemical concentrations in a fluid and, more particularly, various embodiments relate to using light emitting diode systems to determine chemical concentrations in a fluid.

BACKGROUND OF THE INVENTION

Nitrate, $NO_3$, causes eutrophication, illness, and ecological damage in rivers, lakes, estuaries, and oceans. To protect public health, government and private entities often measure nitrate concentrations in various water sources, such as in waste water treatment plants, farms, and industry as well as in supplies like rivers, lakes, and tap water.

One effective method for monitoring nitrate in water involves use of spectroscopy because, like many chemicals, nitrate absorbs light in the ultraviolet range. Specifically, as known by those in the art, as a molecule absorbs light, it is excited from a first, lower energy state to a second, higher energy state. The wavelength of the absorbed light precisely corresponds to the energy difference between the initial state and the excited state, with short wavelength excitation usually being a bond or electronic transition. The energy transition of a bond or electron by optical excitation often is accompanied by molecular vibrational, rotational, or intermolecular energy changes as well. This happens because bond and electronic changes often allow additional vibrational and rotational modes, and greater intermolecular interactions. There are many such modes and interactions and thus, many energy states. Consequently, chemicals generally have broad light absorption peaks, especially in the ultraviolet ("UV") spectrum. Furthermore, the combined electronic, kinetic, and intermolecular excitations of these molecules depend on the bond, molecular shape, and its matrix, which makes it unique for each molecule.

Accordingly, those in the art often use the light absorption of a matrix at different wavelengths of light to determine the concentration of some chemicals in water. Undesirably, however, the light sources typically used for these applications often are complicated, inefficient, and expensive.

SUMMARY OF VARIOUS EMBODIMENTS

In accordance with one embodiment of the invention, a chemical measurement device for determining a concentration of a given chemical in a given fluid has at least one LED light source and at least one light detector. The given chemical has a light absorption curve (referred to simply as "absorption curve") with a peak absorption. The at least one LED light source and the at least one light detector are configured to collaborate to produce two light signals having peak wavelengths spaced between about 5 nm and 35 nm apart. The two light signal peak wavelengths are in the ultraviolet region and are at wavelengths beyond the absorption curve peak. The two light signal peak wavelengths, however, also are before the absorption curve is negligible (i.e., the peak wavelengths correspond to portions of the light absorption curve having a non-zero slope). The device also has a concentration calculator operatively coupled with the at least one light detector. The concentration calculator is configured to compare the two light signals to produce a concentration signal representing the concentration of the given chemical in the given fluid.

In some embodiments, at least two light signal peak wavelengths may be between 220 nm and 280 nm (e.g., to detect nitrite in a fluid). For example, at least one of the two peak wavelengths may be between about 220 nm and 235 nm, while the other of the two peak wavelengths may be between about 235 nm and 280 nm.

The at least one LED light source may include a plurality of LED light sources, or no more than one LED light source. Additionally, or alternatively, the light source may include a UVC laser light source. In a corresponding manner, the at least one light detector may include no more than one light detector or at least two light detectors. Some embodiments include a filter to change the peak wavelength of the at least one light detector and/or a collimator to collimate light emitted by the at least one LED light source. The concentration calculator may be configured to perform a logarithmic operation on the two light signals to produce two signals. As such, the concentration calculator may also have a combiner to combine the two logarithmic signals using a process to determine the concentration of the given chemical.

Using one illustrative form factor, the device may have a housing containing the at least one LED light source and the at least one light detector. As such, the housing forms a fluid channel between the at least one LED light source and the at least one light detector. Preferably, the at least one LED light source and at least one light detector are spaced apart between about 2.5 mm and 25 mm.

In some embodiments, a method determines a concentration of a chemical in a fluid sample. The method provides an LED light source configured to emit ultraviolet light. The method also provides a light detector configured to measure ultraviolet light. A first wavelength and a second wavelength are selected that correspond to portions of an ultraviolet light absorption curve for the chemical in the fluid sample. The first wavelength and the second wavelength are between 5 nm and 35 nm apart. The method emits a first light having an emission spectrum with a peak at the first wavelength and measures the amount of the first light that is absorbed at the first wavelength. The method also emits a second light having an emission spectrum with a peak at the second wavelength and measures the amount of the second light that is absorbed at the second wavelength. The method then determines the concentration of the chemical as a function of the amount of the first light absorbed at the first wavelength and the amount of the second light absorbed at the second wavelength.

In some embodiments, the portions of the ultraviolet light absorption curve are part of a shoulder of the curve. Furthermore, the first wavelength and the second wavelength are selected to both correspond to the same shoulder. For example, the first wavelength and the second wavelength may correspond to areas of the light absorption curve having a negative slope. To help reduce interference, the first light and the second light may have a full width half maximum value of 15 nm or less.

In accordance with another embodiment, a system determines concentrations of a chemical. The system includes a first ultraviolet LED configured to emit light at a first peak wavelength. The system also includes a second ultraviolet LED configured to emit light at a second peak wavelength. The second peak wavelength has a difference of between 5 nm and 20 nm from the first peak wavelength. The system further includes an ultraviolet light detector. A housing contains the first LED, the second LED, and the light detector. The housing forms a fluid channel between the at least one LED light source and the at least one light detector. The fluid channel is configured to hold a fluid having a chemical therein. The system includes a chemical concentration calculator configured to determine the concentration of the chemical in the fluid sample as a function of the absorption of light by the chemical at the first wavelength and the second wavelength.

In some embodiments, the system may include a UV absorption database containing information relating to a UV absorption curve of the chemical. Among other wavelengths, at least one LED is configured to emit light in the UVC spectrum. In some embodiments, the first LED is configured to emit a peak wavelength between about 220 nm and 235 nm. Additionally, the second LED may be configured to emit a peak wavelength between about 240 nm and 255 nm. The LEDs may have a full-width half maximum of less than 15 nm.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 1 schematically shows a cross-sectional view of a chemical concentration measurement device configured in accordance with illustrative embodiments of the invention.

FIG. 2A schematically shows another embodiment using one light emitting diode and two light detectors.

FIG. 2B schematically shows one embodiment using two light emitting diodes and two light detectors.

DESCRIPTION OF ILLUSTRATIVE EMBODIMENTS

Figure 3A:
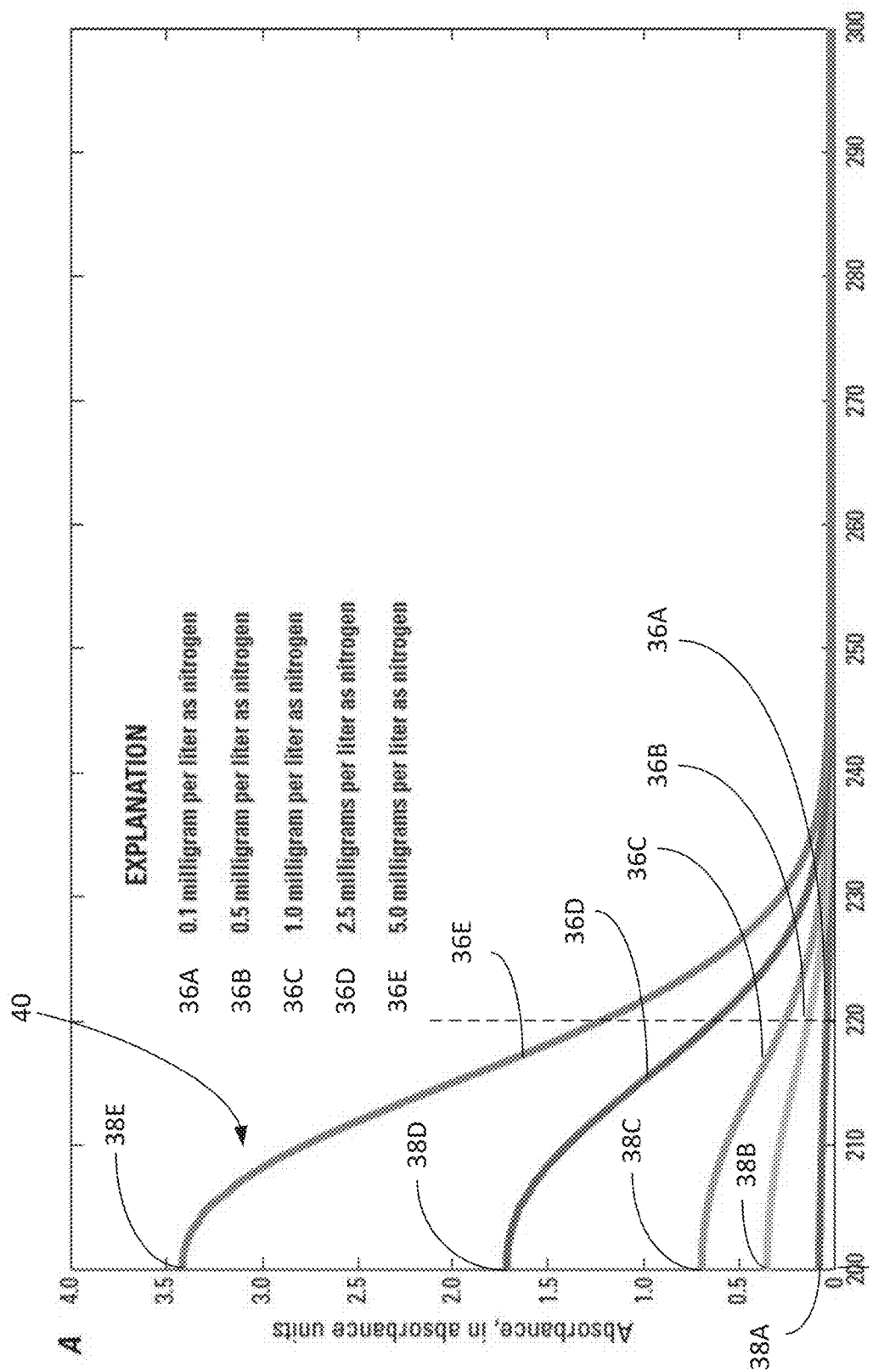
FIG. 3A graphically shows the light absorption curves for various concentrations of a sample analyte in accordance with illustrative embodiments of the invention.

In illustrative embodiments, a chemical measurement device accurately and efficiently measures the concentration of a chemical in a fluid sample. To that end, the device transmits a pair of ultraviolet light signals having similar (i.e., closely spaced on the wavelength scale) peak wavelengths (e.g., between 5 nm and 35 nm apart) through the fluid sample. Throughout the description, these wavelengths may be described as being "closely spaced" or "nearby" to one another. This is not in reference to physical proximity, but instead, refers to closeness of the wavelengths of the wavelength scale (e.g., a wavelength of 250 nm may be said to be nearby or near to a wavelength of 255 nm, but far from a wavelength of 400 nm, regardless of physical proximity).

These two peak wavelengths preferably are at wavelengths larger than wavelength corresponding to the light absorption curve peak (referred to herein as the light absorption peak) of the chemical being tested. Illustratively, that portion of the curve has a relatively steep negative slope. As such, a small difference in peak wavelength should have a significantly different light absorption of the two different light signals. Thus, after comparing the light absorptions of the two light signals, the device can produce a signal representative of the concentration of the chemical in the fluid sample. Other embodiments may have a positive slope and operate in a similar manner. Details of illustrative embodiments are discussed below.

FIG. 1 schematically shows a cross-sectional view of a chemical concentration measurement device 10 configured in accordance with illustrative embodiments of the invention. As shown, the device 10 is in the form of a vial, pipette tip, fluid reactor, or other structure for containing and/or channeling fluid, such as water, within its interior. To that end, the device 10 has a housing 12 that forms an interior fluid chamber or channel 14 between a top end and a bottom end (from the perspective of FIG. 1). Either end may be open to receive fluid. For example, the top end may be open to receive a poured fluid, or the bottom end may be open to draw the fluid upwardly by a vacuum (not shown).

The channel 14 contains functional components that cooperate to detect chemicals and identify their concentrations within a larger fluid. Specifically, the channel 14 includes a set of one or more LED light sources ("LEDs 16"), a set of one or more light detectors 18, and a concentration calculator 20 for comparing and/or processing output signals from the detectors 18. In preferred embodiments, the LEDs 16 and detectors 18 cooperate to produce a pair of light signals, shown schematically by the two generally parallel arrows pointing from the LEDs 16 to the detectors 18. As discussed below, those two signals are processed to determine chemical concentrations in the fluid of a prescribed chemical. Although shown simultaneously, it should be understood that the light signals may be produced simultaneously or at different times. Additionally, each of the light signals may be produced by the same or different LEDs 16. Therefore, illustrative embodiments may use a single LED 16 to perform the same or similar process as described herein.

The inventors recognized that light absorption of a matrix at varying light wavelengths can be a good indicator of the concentration of some chemicals. For example, nitrate in water absorbs most at around 210 nm, and continues to absorb up to around 255 nm. This phenomenon occurs because the shape of the slope of absorbance between 200 nm and 250 nm is specific to nitrate ions dissolved in water. Accordingly, the inventors recognized that by measuring the light absorption spectrum of a water sample, for example, it is possible to calculate the concentration of nitrate in the sample.

It should be noted that while illustrative embodiments are discussed in terms of nitrate, alternative embodiments apply to other chemicals in water and/or other fluids (e.g., liquids, gasses, etc.). Accordingly, discussion of nitrate is by example and not intended to limit various other embodiments of the invention.

To assess the light absorption spectrum of a sample, a light source, monochromator, and detector; or a light source, diffractometer, and detector array may be used. Prior art light sources for these spectroscopic measurements typically include xenon lamps or deuterium lamps, which emit a broad spectrum of light. These systems can measure the light absorption spectrum nearly continuously and thus, provide high measurement accuracy in complex matrixes. However, because they combine moving, difficult to fabricate, and complex components, they often are too expensive for many applications. Accordingly, some embodiments perform discrete measurements of light absorption at particular wavelengths (i.e., as opposed to continuous wavelength spectrum measurements, which require larger and complex equipment).

Illustrative embodiments reduce complexity and thus, cost, by measuring only parts of the spectrum, eliminating the need for monochromators, diffractometers, and detector arrays. Other instruments may use photodetectors with specific absorption ranges, either due to their material properties or specialized filters, to measure specific wavelengths. Other methods use lasers and mercury lamps, which emit in a narrow wavelength range. These methods are accessible and inexpensive, but because there are many molecules that absorb light in a matrix, selection of the appropriate wavelengths for such systems is important. In the prior art known to the inventors, typically one wavelength that an analyte absorbs is selected, and additional wavelengths are selected that are absorbed by common interfering molecules, but not by the chemical of interest. This works well for known or controlled samples, is grounded in traditional experimental chemistry, and is reinforced by limitations in light source, detectors, and filters. Unfortunately, in systems with widely varying matrix components and many different molecules, significant error limits effectiveness.

Against these challenges, the inventors recognized that using LEDs 16 as light sources, including in the UVC wavelength range (<280 nm), makes them a candidate for measuring nitrate, among other chemicals. LEDs 16 emit light at a "sweet spot"—with a wider light-emission spectrum than lasers or mercury lamps, but narrower than xenon or deuterium lamps. Additionally, LEDs 16 provide a large variety of selectable center wavelengths. Accordingly, by using LEDs 16, detectors 18 can measure average absorbance over a narrow range of wavelengths (as compared to some other light sources). For example, some LEDs 16 may have a FWHM of roughly 15 nm (i.e., the wavelength range where the output light is half of its peak 33 or 35 value), which is well suited for the UV spectrum.

Xenon flash lamps and deuterium lamps emit a very wide range of UV light. Thus, optical filters are applied to measure only desired wavelengths in the spectra of UV light for desired absorption measurement. For mercury lamps, emission peaks are even sharper than LEDs 16, but expensive optical filters are required for a different reason: mercury lamps emit multiple wavelengths in the UV range. For example, emission wavelengths from mercury lamp are well known (e.g., 185 nm, 254 nm, 313 nm, 365 nm, etc.). Accordingly, when using mercury lamps, to extract only 254 nm, an optical filter is applied to screen out 185 nm, 313 nm, 365 nm, etc. LEDs 16 provide an advantage in that the emission wavelength is "tunable" (e.g., by changing the chemical composition of the semiconductor light emission layer). In contrast, mercury lamps are bound by excitation energy levels of mercury atoms.

Illustrative embodiments provide the advantage that LED 16 light sources emit a relatively narrow band of wavelengths. In some embodiments, the LED 16 emits a FWHM of 15 nm or less. In some other embodiments, the LED 16 emits a FWHM of 20 nm or less. Preferably, the FWHM range is within the ultraviolet range (e.g., in the UVC wavelength range). Furthermore, illustrative embodiments of the LED 16 emit a single peak wavelength at a time, as opposed to other light sources that emit multiple peaks in various wavelengths. Preferably, the LED 16 emits the peak in the UV range (e.g., in the UVC range). Limitations on the state of the art have made it difficult to produce UV range laser emissions. However, as the state of the art improves, it is contemplated that various embodiments may use lasers (e.g., UVC lasers) as a light source in addition, or alternatively, to the LED 16. Illustrative embodiments may use light sources including AlN substrates (e.g., fabricated on bulk single-crystal AlN substrates). Such light sources (including UVC lasers) may be used in addition, or alternatively, to the LEDs 16 described herein.

Illustrative embodiments also provide the advantage of a simplified system as compared to more complex spectroscopy devices. For example, illustrative embodiments use a few discrete wavelengths having small differences in their peak wavelengths, whereas spectroscopy uses continuous spectra in a certain range of wavelengths. Illustrative embodiments thus provide for a much more cost effective, compact, light-weight, and simpler structure that is mechanically robust, and uses considerably less power consumption than spectroscopy. Additionally, illustrative embodiments determine concentrations of known or suspected target chemicals in fluid, as opposed to spectroscopy which provides a system for identifying mixtures of multiple unknown chemicals. To that end, illustrative embodiments choose LED 16 emission wavelengths that correspond to the known absorption curve (e.g., the shoulder) of the target chemical.

Contrary to expectations and traditional methods, the inventors discovered that a useful control in many complex matrixes for interfering ions is in the shoulder of the light absorption curve of the analyte (discussed below with regard to FIG. 3C)—not measuring specific interferences. This is because such a wavelength provides significant information about a vast number of interfering molecules, while absorbing much less light from the analyte relative to the measurement in the full absorbing region.

Some applications include an optical filter 22 in the light path of an LED 16 to one of two detectors 18, which transmits only light of a desired wavelength range. Since the LEDs 16 emit a relatively wide range of wavelengths, with carefully selection of the cut-off wavelength of the optical filter 22, shorter and/or longer wavelengths may be blocked. For example, the cut-off wavelength of the optical filter 22 can be between 220 nm and 240 nm.

Another detector 18 without such filter 22 detects signals from the entire emission spectrum. Subsequently, the difference in the signal from these two detectors 18 can be used to assess these two nearby wavelengths to determine the concentration of a chemical that absorbs in the wavelength range covered by emission spectra of the LED 16. This not only measures two wavelengths near to each other, but also reduces the compounding error of multiple light sources.

For example, FIG. 2A schematically shows a pair/arrangement with only one LED 16 that emits light with a wavelength peak (e.g., at 235 nm) and two detectors 18 for detecting the emitted light. One of the detectors 18 has a high-pass pass filter 22 with an edge at 235 nm while the other detector 18 has no filter 22. Both detectors 18 are arranged so that the light from the LED 16 is incident on both detectors 18. In such a system, the difference in signal between these two detectors 18 can be used to assess the absorbance of a sample at two similar wavelengths and thus, determine nitrate concentration. In addition, the system of FIG. 2A also can have a lens 24 to collimate the LED 16 light.

FIG. 2B schematically shows a similar embodiment having two LEDs 16 and two detectors 18. No filter 22 is necessary in this example (although it could be added) because the two LEDs 16 preferably have two different peak wavelengths. As with the other embodiment, the two light signals produced/detected by the detectors 18 of FIG. 2B have close peak wavelengths and are close to each other in the UV spectrum. It should be understood that the embodiments shown in FIGS. 2A-2B are merely illustrative. There are other arrangements and quantities of LEDs 16 and detectors 18 that may be used. For example, some embodiments may use a single LED 16 and a single detector 18.

One skilled in the art can select the peak wavelengths as a function of the chemical being tested. Preferably, those wavelengths are relatively close to each other so that they intersect the light absorption curve after the peak of the light absorption curve (i.e., on the downward slope of the light absorption curve). Thus, in some embodiments, the chemical of interest to be tested for is known in advance. Accordingly, appropriate selection of the peak wavelengths may be made. Additionally, some embodiments may include to measure a third absorbance from a third distant wavelength, such as 350 nm, to measure turbidity in water. However, this third distant wavelength is generally too far from the shoulder of the light absorption curve to function as the first or second wavelength used to determine concentrations.

FIG. 3A shows light absorption curves 36A-36E for various concentrations of a sample analyte, in this case, nitrate. As expected, in general, the higher the concentration of the molecule in water, the larger the absorbance of light. Although the curves 36A-36E shown are for nitrate (NO3), it should be understood that similar principles apply for a variety of different chemicals.

The curves 36A-36E also represent the KNO3 molecule dissolved in water. This is because KNO3 dissolved in water generates NO3− ion and K+ ion. Thus, effectively KNO3 and NO3− ion are the same in terms of UV absorption in water. Furthermore, NO3 is provided as one example of a chemical compound that can be detected by illustrative embodiments of the invention.

As seen from the graph, nitrogen at a plurality of concentrations has a peak absorption wavelength 37 of around 200 nm. Wavelengths greater than the peak absorption wavelength 37 have less absorption, and thus, slope negatively on the absorption curves 36A-36E. These portions of the absorption curve 36 adjacent the peak absorption 38A-38E may be referred to as a shoulder 40 portion of the curve 38A-38E. The shoulder 40 includes the wavelengths between the peak wavelength 37 and the plateau point as measured by the detector 18 (e.g., where absorbance is less than 1% to 2% of the peak absorption 38A-38E value for the respective curve 36A-36E). As detectors 18 improve, and without turbidity or interfering chemical species, the absorption signal of the target chemical may be determined at higher sensitivities and farther from the absorption peak wavelength 37. However, considering the signal to noise ratio of state of the art detectors 18, 1% to 2% is generally the smallest absorption signal that may be detected. A second shoulder 40 exists on the other side of the peak wavelength 37, but is not visible in FIG. 3A.

Furthermore, although various concentrations of the same molecule share the same peak absorption wavelength 37, the concentration of the chemical impacts the total absorbance (e.g., each curve 36A-36E has a corresponding absorption peak value 38A-38E). Accordingly, in some embodiments the absorption values may be used not only to detect concentrations of known chemical(s) in sample, but also to identify the chemical in the sample.

Figure 3B:
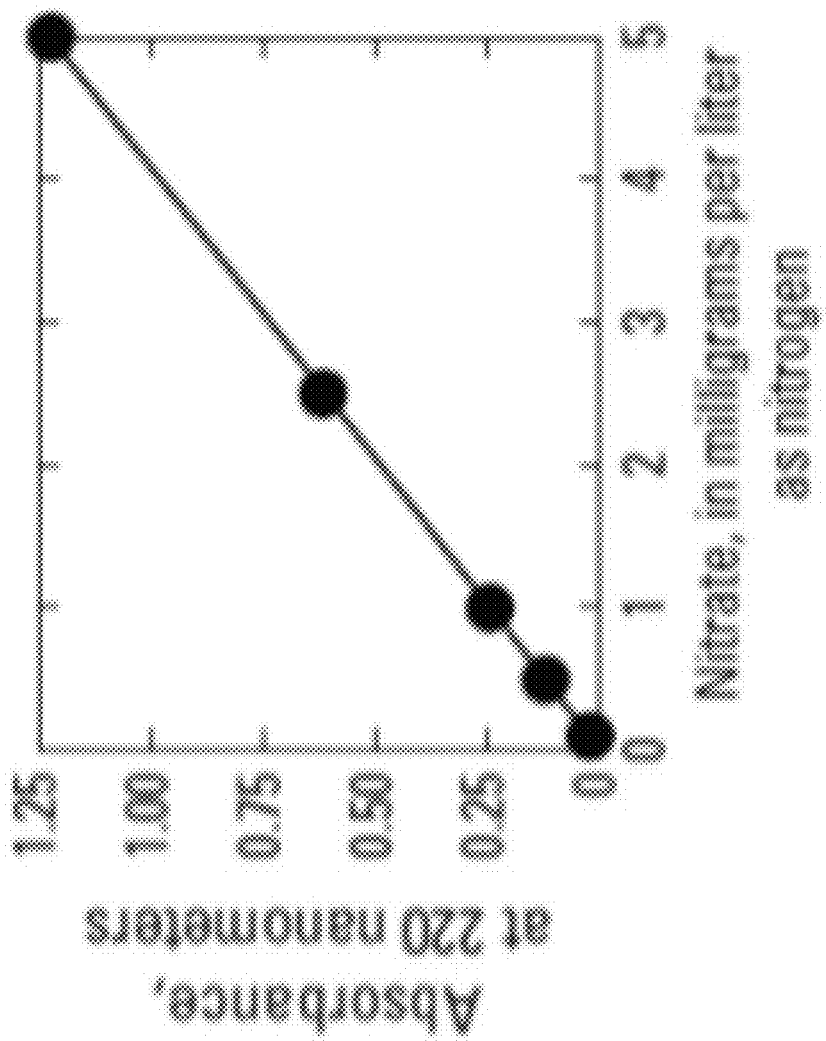
FIG. 3B graphically shows the relationship between absorbance values at 220 nm wavelength for the various concentrations of analyte shown in FIG. 3A.

FIG. 3B graphically shows the relationship between absorbance values at 220 nm wavelength for the various concentrations of nitrate shown in FIG. 3A. Some chemical compounds, such as nitrate, have a generally linear relationship between absorbance at a particular wavelength and concentration of the compound. Illustrative embodiments may use this known relationship, among other things, to determine the concentration of the chemical based on absorbance.

Figure 3C:
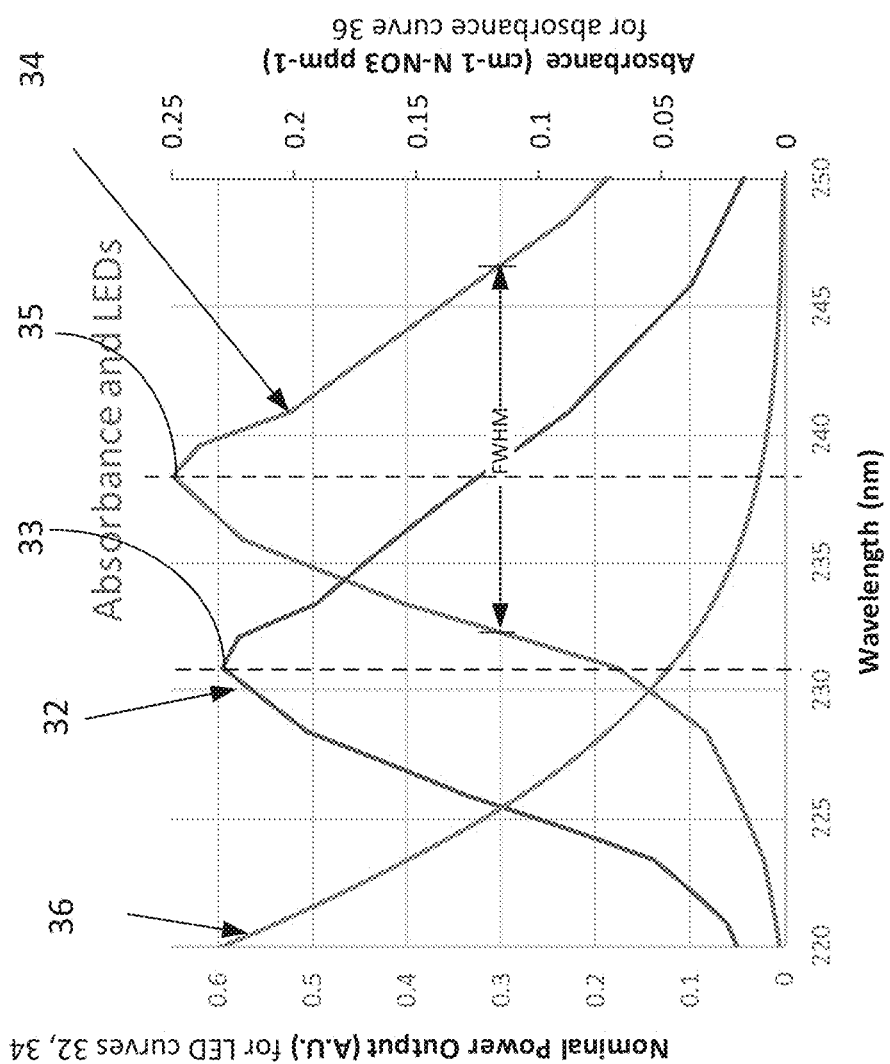
FIG. 3C graphically shows the light emission spectrums of two light emitting diodes and an exemplary light absorption curve of nitride in accordance with one embodiment of the invention.

FIG. 3C graphically shows two exemplary LED 16 light emission curves 32, 34 plotted relative to the light absorption curve 36 of a chemical, in this example, nitrate. The values for the light absorption curve are shown using a "nominal power output" unit. This is because, as shown in FIG. 3A, the light absorption curve has different values for different concentrations of the chemical. However, the absorption curves 36A-36E have the same peak wavelength 37 and generally have similar shape regardless of concentration (i.e., with a scaled variance in amplitude). As mentioned previously, the light emission curves 32 and 34 may be output by two LEDs 16 (e.g., simultaneously), and/or a single LED 16 (e.g., sequentially). As shown in FIG. 3C, the LED(s) 16 output the first light emission curve 32 with a peak wavelength 33, and the second light mission curve 34 with a peak wavelength 35.

LEDs 16 are configured to output peaks at target wavelengths 33, 35 (also referred to as peak 33 and peak 35). Furthermore, although the LED 16 is configured to output a particular peak 33, 35 output, the LED 16 also outputs light in a spectrum of wavelengths around the peak 33, 35, but at lower intensities. For example, in FIG. 3C the first LED 16 is set to output light at 231 nm peak 33 wavelength. The light emission curve 32 thus shows the peak 33 output corresponding to 231 nm, in addition to other wavelengths in the light-emission spectrum. The second LED 16 is set to output light a peak 35 of 238 nm wavelength. The light emission curve 34 thus shows a peak 35 output corresponding to 238 nm, in addition to other wavelengths in the light-emission spectrum.

The portion of the light absorption curve 36 shown is after the peak absorption wavelength 37 for NO3 (i.e., FIG. 3C shows absorption wavelengths that are larger than the peak light absorption wavelength 37 of the light absorption curve 36). To produces significantly different signals with a relatively small change in peak wavelength 33 and 35, illustrative embodiments emit two light signals that both intersect the light absorption curve at a portion that has a relatively large slope value (e.g., large negative slope or large positive slope). Indeed, both peak wavelengths likely may not be as useful if both were in the higher wavelengths that approach a negligible light absorption (e.g., greater than about 245 in this example, which has a relatively flat slope). To highlight this, FIG. 3C has a pair of vertical dashed lines to show the intersections of the peak wavelengths 33, 35 with a portion of the sloping part of the light absorption curve 36.

In illustrative embodiments, for nitrate, the two peak light emission wavelengths are between about 200 nm or 220 nm and 280 nm. For example, one of the two peak wavelengths may be between about 220 nm and 235 nm and the other of the two peak wavelengths may be between about 235 nm and 280 nm. In preferred embodiments, the two peak wavelengths are spaced between about 5 nm and 35 nm apart within that range (e.g., about 231 nm and 238 nm as in FIG. 3). If the peaks 33, 35 are too close, then they may not have enough resolution for a meaningful result. In other words, it is difficult to accurately measure the difference in absorbance given the current state of detectors 18. To that end, in illustrative embodiments, the peak wavelengths are at least 1 nm, at least 2 nm, at least 5 nm, at least 10 nm, at least 15 nm, or at least 20 nm apart.

On the other hand, in some embodiments, if the peaks 33, 35 are too far, then it is possible that the wavelength approaches the absorption curve 36 and the absorption peak 38 of another chemical, and interference from the other chemical becomes significant. To that end, in illustrative embodiments, the peak wavelengths 33, 35 of the two LED 16 emissions are at most 20 nm apart. Additionally, it is possible that if the peak 33, 35 wavelengths are too far apart that the highly sloped portion of the absorption curve 36 may be missed entirely by the measurement. Accordingly, illustrative embodiments maintain the peak 33, 35 wavelengths within 35 nm of one another.

It should be noted that a negligible light absorption on the light absorption curve 36 may be considered to occur when the light wavelengths are at a point in which light absorption of the chemical of interest is below the detection limit of a measurement system. For example, wavelengths at the 1.0 or 2.0 percent level and lower on the light absorption curve 36 may qualify as being negligible. Those skilled in the art can determine the levels that are considered negligible.

As noted above, other embodiments apply to the positive sloped portion of the absorption curve 36 (not shown in FIG. 3C). Accordingly, principals discussed above with regard to the negative sloped portion also apply to the positive sloped portion in various embodiments. It should be noted that currently it is difficult to manufacture LEDs 16 having less than 200 nm wavelength peak output. Therefore, as a practical matter, illustrative embodiments may apply to the negatively sloped portion of some chemical absorption curves 36.

Moreover, the detector(s) 18 and LED(s) 16 preferably are spaced a prescribed distance apart so that they are not too close to saturate the detectors 18, and still not too far away to produce an inadequate signal. For example, with specified low power LEDs 16, the distance can be between about 2.5 mm and about 25 mm. Indeed, those skilled in the art can tune the distance to comply with lumens, power, fluid, chemical, fluid channel turbulence and diameter, etc. of the device 10.

Some prior art, such as lamps, emit light in a radially outward direction (e.g., from a cylindrical lamp). In contrast, in some embodiments the LEDs 16 provide a more targeted output of light towards the detector 18. Lamps may also add further computational and configuration complexity. For example, in order to capture all of the light emitted by the lamp, the one or more detectors 18 must surround the lamp. Alternatively, if the detector 18 does not surround the lamp, a substantial portion of the light output is directed away from the detector 18 and reflects and/or is absorbed by other surfaces. Accordingly, in some embodiments, the detectors 18 are positioned near the LED 16 so as to be positioned substantially within a radiation emission cone of the LED 16.

As noted, some embodiments have equal numbers of light detectors 18 and LEDs 16, and different numbers of those elements. Some have multiple sets of those elements. Accordingly, some embodiments can have more than one or two LEDs 16/detectors 18 sets, such as third, fourth, etc. Effective use of filters 22 can facilitate use of fewer LEDs 16 and/or detectors 18.

As noted, the analyte can be an aqueous solution, air, or other gas phase material. In illustrative embodiments, light emitted by the LEDs 16 passes through a matrix and is incident on the detectors 18. For example, two pairs of LED and a detector sets 16/18 cooperate with the concentration calculator 20 for electronic comparison. Among other ways, some embodiments use the logarithm of the difference in signal with and without the analyte from each detector 18 to indicate the magnitude of light absorption in relevant wavelength ranges. These absorbances should be compared to a calibration curve in which many similar matrixes with varying, known levels of the analyte. Other embodiments may use other techniques.

Signals from such detectors 18 can be converted to numerical values by using an analog to digital converter, stored in memory in the system, where an algorithm determines the target chemical concentration. In some embodiments, signals from detectors 18 of solutions of known chemical concentration can be stored in the memory and used as part of a calibration curve.

Figure 4:
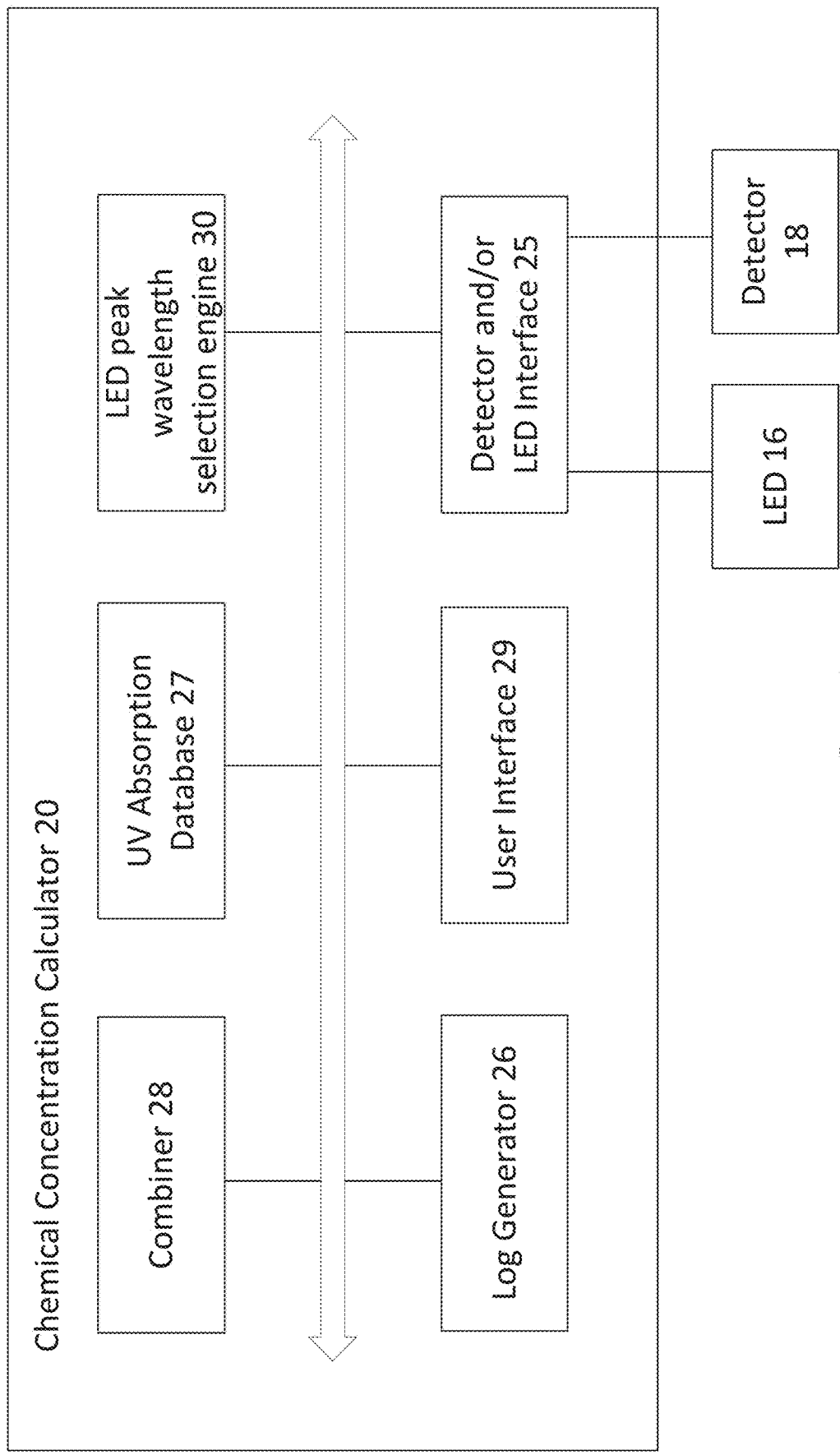
FIG. 4 schematically shows an exemplary implementation of a chemical concentration calculator in accordance with illustrative embodiments.

FIG. 4 schematically shows one exemplary implementation of a chemical concentration calculator 20 in accordance with illustrative embodiments. Each of the components of the concentration calculator 20 is operatively connected by any conventional interconnect mechanism. FIG. 4 simply shows a bus communicating each the components. Those skilled in the art should understand that this generalized representation can be modified to include other conventional direct or indirect connections. Accordingly, discussion of a bus is not intended to limit various embodiments.

Indeed, it should be noted that FIG. 4 only schematically shows each of these components. Those skilled in the art should understand that each of these components can be implemented in a variety of conventional manners, such as by using hardware, software, or a combination of hardware and software, across one or more other functional components. For example, the combiner 28 (discussed below) may be implemented using a plurality of microprocessors executing firmware. As another example, the combiner 28 may be implemented using one or more application specific integrated circuits (i.e., "ASICs") and related software, or a combination of ASICs, discrete electronic components (e.g., transistors), and microprocessors. Accordingly, the representation of the combiner 28 and other components in a single box of FIG. 4 is for simplicity purposes only. In fact, in some embodiments, the combiner 28 of FIG. 4 is distributed across a plurality of different machines—not necessarily within the same housing or chassis. In addition, some components of the calculator 20 may be separate from the calculator 20. For example, the UV absorption database may be separate from the calculator 20.

It should be reiterated that the representation of FIG. 4 is a significantly simplified representation of an actual chemical concentration calculator 20. Those skilled in the art should understand that such a device has many other physical and functional components, such as central processing units, other packet processing modules, and short-term memory. Accordingly, this discussion is in no way intended to suggest that FIG. 4 represents all the elements of the chemical concentration calculator 20.

Moreover, although FIG. 1 shows the concentration calculator 20 within the housing 12 of the device 10, some embodiments may position the concentration calculator 20 in part or entirely exterior to the device 10. Such embodiments, as well as other embodiments, thus may have an interface 30 or mechanism for communicating with the concentration calculator 20.

The calculator 20 includes a user interface 29 configured to receive input from a user (e.g., via a keyboard, a mouse, and/or a network enabled smartphone device). In some embodiments, the calculator 20 may have a Bluetooth enabled or wireless internet connection. Through the interface 29, the user may select a chemical of interest to measure. After the chemical of interest (also referred to as the analyte) is selected, the calculator 20 communicates with a chemical absorption database 27. The chemical absorption database 27 contains data relating to the UV absorption curve (or portions thereof) for the selected chemical (e.g., absorption curves 36A-36E for nitrogen). The data relating to the UV absorption curve 36 is communicated to an LED peak wavelength selection engine 30. The peak wavelength selection engine 30 selects two appropriate peak wavelengths for emission by the LED(s) 16, preferably that correspond to the highly sloped portion of the UV absorption curve 36 of the chemical.

The concentration calculator 20 includes a detector and/or LED interface 25 configured to communicate with one or more of the LEDs 16 and/or detectors 18. After the wavelengths are selected (e.g., by the selection engine 30 or by the user), the appropriate LEDs 16 are activated to emit light at the selected wavelengths. The signal may be sent through the interface 25. Additionally, or alternatively, the signals detected by detectors 18 may be communicated to the calculator 20 via the interface 25.

The concentration calculator 20 includes a log generator 26 configured to convert the signals from the detector(s) 18 into logarithmic signals that are processed by combining logic, such as a combiner 28. The combiner 28 thus combines the signals to produce a signal indicative of the chemical concentration in the fluid.

In one embodiment, an optical filter 22 that blocks one portion of the spectrum is applied on top of one detector 18. Another filter 22 with different optical properties may be used on another detector 18. For example, nitrate in water can be measured with an LED 16 having a peak at 235 nm as the light source. Light passes through the sample, and then a filter 22 that passes only light with wavelengths shorter than 235 nm on one detector 18, and also through another filter 22 that passes only greater than 235 nm on another detector 18. In this case, the difference in the signals from the two detectors 18 can be used to determine the nitrate concentration in the solution because 235 nm is within the negative slope of light absorption peak from nitrate ions in water.

Figure 5:
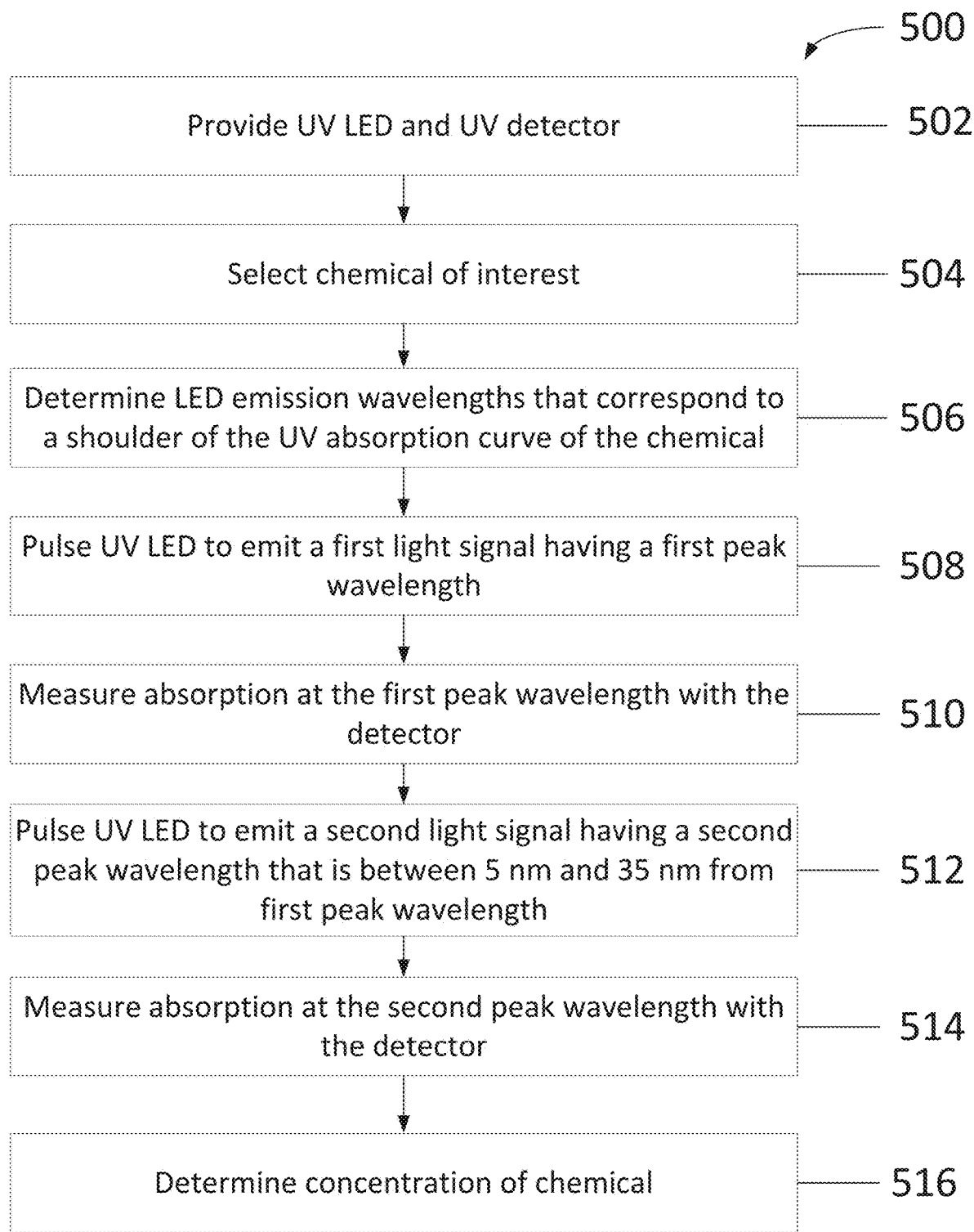
FIG. 5 shows a process of determining the concentration of the chemical in accordance with illustrative embodiments of the invention.

FIG. 5 shows a process 500 of determining the concentration of the chemical in accordance with illustrative embodiments of the invention. The process begins at step 502, which provides the one or more UV LEDs 16 and the one or more UV detectors 18. As described previously, the UV LEDs 16 may of the type that emit radiation in the UVC wavelength. Additionally, the UV LEDs may be configured to output peak wavelengths 33, 35 that are between 5 nm and 35 nm apart. Additionally, in some embodiments, the LEDs 16 have a FWHM that is less than about 15 nm (e.g., from about 225 nm to about 240 nm). The detector 18 in a corresponding manner is configured to detect UV-spectrum light.

At step 504, a chemical of interest is selected. Illustrative embodiments determine the concentration of the selected chemical. In some embodiments, the user may actively select the chemical of interest (e.g., through the user interface 29). Alternatively, in some other embodiments, the user may merely determine the chemical of interest. Regardless, after the chemical is determined, the UV absorption curve 36 of the chemical, or portions thereof, are accessed.

At step 506, by accessing the absorption curve 36, two appropriate LED emission peak wavelengths may be selected. As described previously, the LED emission peak wavelengths 33, 35 are preferably on a largely sloped portion of the UV absorption curve, such that small changes in wavelength result in relatively large changes in UV absorption values. To that end, the wavelengths may be between 5 nm and 35 nm apart. Preferably, the selected wavelengths are between 5 nm and 20 nm apart.

The process then proceeds to step 508, which pulses the UV LED to emit a first light signal having a first peak wavelength. The first peak wavelength is determined in the previous step. Preferably the emitted light signal has a FWHM of about less than 15 nm. This helps reduce interference from nearby emission wavelengths. The process then proceeds to step 510, which measures the UV absorption at the first peak wavelength with the detector 18.

At step 512, the process pulses the UV LED 16, which may be the same or a different LED from step 508, to emit a second light signal having a second peak wavelength. The second peak wavelength is determined at step 506. As described previously, the second peak wavelength is preferably of a UV wavelength that is between 5 nm and 35 nm apart from the first peak wavelength emitted in step 508. The process then proceeds to step 514, which measures the absorption at the second peak wavelength with the detector 18.

The process then proceeds to step 516, which determines the concentration of the selected chemical by comparing absorption at first peak wavelength with absorption at second peak wavelength. Various concentrations of a particular chemical correspond to known various absorption curves. As shown in FIG. 3A, for example, the absorption curves 36 for various concentrations may have some known relationship (e.g., a linear relationship where concentrations of 5 mg of nitrogen per liter has 5× the absorbance of concentrations of 1 mg of nitrogen per liter). Using the data relating to the absorption curves 36, the method compares the absorption values from the first light signal and the second light signal, and determines the concentration of the chemical.

It should be noted that the process 500 is a simplified version of a more complex process of determining the concentration of the chemical. As such, the actual process may have additional steps that are not discussed. In addition, some steps may be performed in a different order, or in parallel with each other. For example, steps 508 and 512 may be performed simultaneously. Accordingly, discussion of this process is illustrative and not intended to limit various embodiments of the invention.

The embodiments of the invention described above are intended to be merely exemplary; numerous variations and modifications will be apparent to those skilled in the art. Such variations and modifications are intended to be within the scope of various embodiments as defined by any of the appended claims.

The invention claimed is:

1. A chemical measurement device for determining a concentration of a given chemical in a given fluid, the given chemical having a light absorption curve with a peak, the device comprising:
   at least one LED light source;
   at least one light detector,
   the at least one LED light source and at least one light detector configured to produce two light signals having peak wavelengths between about 5 nm and 35 nm apart, the two light signal peak wavelengths being in the ultraviolet region and at wavelengths greater than the light absorption curve peak wavelength, the two light signal peak wavelengths corresponding to before the light absorption curve is negligible; and
   a concentration calculator operatively coupled with the at least one light detector, the concentration calculator configured to compare the two light signals having peak wavelengths between about 5 nm and 35 nm apart to produce a concentration signal representing the concentration of the given chemical in the given fluid.

2. The device of claim 1, wherein the at least two light signal peak wavelengths are between 220 nm and 280 nm.

3. The device of claim 1, wherein the at least one LED light source comprises a plurality of LED light sources.

4. The device of claim 1, wherein the at least one LED light source comprises no more than one LED light source.

5. The device of claim 1, wherein the at least two light detectors.

6. The device of claim 5, further comprising a filter to change the peak wavelength of the at least one light detector.

7. The device of claim 1, further comprising a UVC laser light source.

8. The device of claim 1, further comprising a collimator to collimate light emitted by the at least one LED light source.

9. The device of claim 1, wherein the concentration calculator is configured to perform a logarithmic operation on the two light signals to produce two signals, the concentration calculator having a combiner to combine the two signals to determine the concentration of the given chemical.

10. A method of determining a concentration of a chemical in a fluid sample, the method comprising:
    providing an LED light source configured to emit ultraviolet light, and a light detector configured to measure ultraviolet light;
    selecting a first wavelength and a second wavelength that correspond to portions of an ultraviolet light absorption curve for the chemical in the fluid sample, the first wavelength and the second wavelength being between 5 nm and 35 nm apart;
    emitting a first light having an emission spectrum with a peak at the first wavelength;
    measuring the amount of the first light that is absorbed at the first wavelength;
    emitting a second light having an emission spectrum with a peak at the second wavelength;
    measuring the amount of the second light that is absorbed at the second wavelength;
    determining the concentration of the chemical as a function of the amount of the first light absorbed at the first wavelength and the amount of the second light absorbed at the second wavelength.

11. The method as defined by claim 10, wherein the portions of the ultraviolet light absorption curve are part of a shoulder of the ultraviolet light absorption curve.

12. The method as defined by claim 11, wherein the first wavelength and the second wavelength are selected to both correspond to the same shoulder.

13. The method as defined by claim 10, wherein the first light and the second light having a full width half maximum value of 15 nm or less.

14. The method as defined by claim 10, wherein the first wavelength and the second wavelength correspond to areas of the light absorption curve having a negative slope.

15. The method as defined by claim 10, wherein the at least one LED and the light detector are spaced apart between about 2.5 mm and 25 mm, the method further comprising forming a fluid channel between the LED light source and the light detector.

16. A system for determining concentrations of a chemical, the system comprising:
    a first ultraviolet LED configured to emit light at a first peak wavelength;
    a second ultraviolet LED configured to emit light at a second peak wavelength, the second peak wavelength having a difference of between 5 nm and 20 nm from the first peak wavelength;
    an ultraviolet light detector;
    a housing containing the first LED, the second LED, and the light detector, the housing forming a fluid channel between the at least one LED light source and the at least one light detector, the fluid channel configured to hold a fluid having a chemical therein;
    a chemical concentration calculator configured to determine the concentration of the chemical in the fluid sample as a function of the absorption of light by the chemical at the first wavelength and the second wavelength.

17. The system as defined by claim 16, wherein the first LED is configured so that the first peak wavelength is between about 220 nm and 235 nm and the other of the two peak wavelengths is between about 240 nm and 255 nm.

18. The system as defined by claim 16, further comprising a UV absorption database containing information relating to a UV absorption curve of the chemical.

19. The system as defined by claim 16, wherein the housing comprises a vial, a pipette tip, or a fluid reactor.

20. The system as defined by claim 16, further comprising a UVC laser light source.

* * * * *